United States Patent [19]
Johnson et al.

[11] Patent Number: 5,609,641
[45] Date of Patent: Mar. 11, 1997

[54] TIBIAL PROSTHESIS

[75] Inventors: Chris E. Johnson; Thomas A. Carls, both of Memphis; David L. Evans, Bartlett, all of Tenn.

[73] Assignee: Smith & Nephew Richards Inc., Memphis, Tenn.

[21] Appl. No.: 381,118

[22] Filed: Jan. 31, 1995

[51] Int. Cl.$^6$ ........................................... A61F 2/38
[52] U.S. Cl. ................................. 623/20; 623/18
[58] Field of Search ..................... 623/16, 17, 18, 623/19, 20, 21, 22, 23

[56] References Cited

U.S. PATENT DOCUMENTS

| | | | |
|---|---|---|---|
| 2,934,065 | 4/1960 | Townley | 623/23 |
| 3,064,645 | 11/1962 | Ficat et al. | 623/23 |
| 4,016,606 | 4/1977 | Murray et al. | 623/20 |
| 4,479,271 | 10/1984 | Bolesky et al. | 623/20 |
| 4,759,767 | 7/1988 | Lacey | 623/20 |
| 4,936,853 | 6/1990 | Fabian et al. | 623/20 |
| 4,938,769 | 7/1990 | Shaw | 623/20 |
| 4,944,757 | 7/1990 | Martinez et al. | 623/20 |
| 5,002,578 | 3/1991 | Luman | 623/18 |
| 5,108,434 | 4/1992 | Ahmens | 623/18 |
| 5,116,375 | 5/1992 | Hofmann | 623/20 |
| 5,137,536 | 8/1992 | Koshino | 623/20 |
| 5,246,459 | 9/1993 | Elias | 623/20 |

FOREIGN PATENT DOCUMENTS

| | | | |
|---|---|---|---|
| 493526 | 2/1950 | Belgium | 623/23 |
| 4320086 | 12/1994 | Germany | 623/23 |
| 2192543 | 1/1988 | United Kingdom . | |
| 2253147 | 9/1992 | United Kingdom | 623/20 |

OTHER PUBLICATIONS

P. F. C.® Modular Porous Coated Tibial Tray With Screws, Surgical Technique, Johnson & Johnson Orthopaedics.

P.F.C.® Long Stem with Specialist® Instruments, Revisional Surgical Technique, Johnson & Johnson Orthopaedics.

*Primary Examiner*—David Isabella
*Attorney, Agent, or Firm*—Pravel, Hewitt, Kimball & Krieger

[57] ABSTRACT

A tibial prosthesis includes a tibial tray and a post extending therefrom for receiving one or more modular stems of differing sizes. The stem provides a closed socket that registers with the post. A wedge lock fit tightens the stem to the post upon assembly. The stem has a cylindrical section and a tapering section. Fins extend longitudinally from the proximal end to the distal end of the stem, tracking both the cylindrical and tapering portion thereof so that each of the fins tracks a uniform diameter section of the stem for a majority of its length. The tapering section of the stem is equal to about one third of its over all length, and defines the distal end of the stem. The fins are longitudinally placed about the stem exterior surface, and are generally parallel. Between the fins are U-shaped channels that are similarly longitudinally extending and generally parallel. The stem provides a central longitudinal axis. The fins and channels are parallel to the central longitudinal axis of the stem.

33 Claims, 5 Drawing Sheets

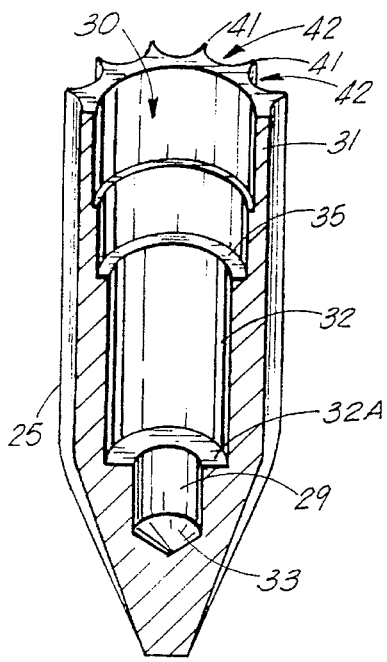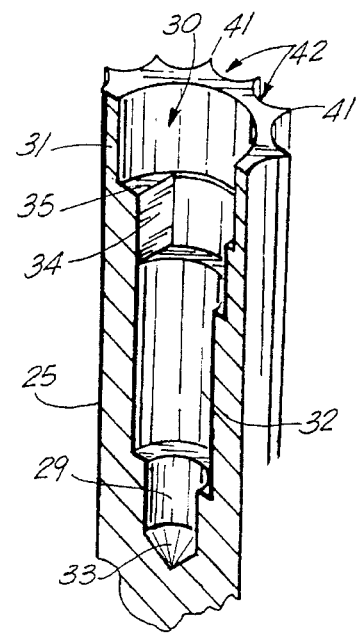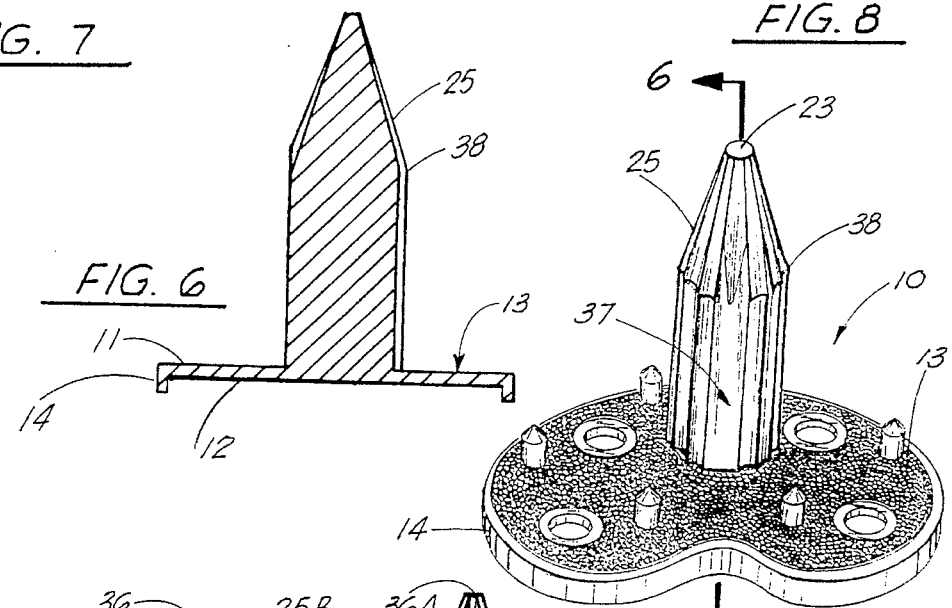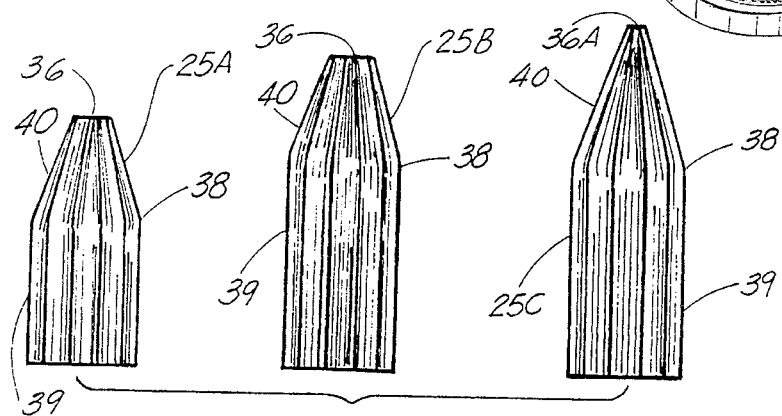

TIBIAL PROSTHESIS

BACKGROUND OF THE INVENTION

1. Field of the Invention

The present invention relates to orthopedic prosthetic devices and more particularly to an improved prosthesis for replacing a portion of a patient's knee joint. Even more particularly, the present invention relates to an improved tibial prosthesis that is modular, having a removable metaphyseal stem portion that includes a cylindrical section and a tapering section, and wherein parallel fins extend continuously from the proximal to the distal end of the metaphyseal stem, tracking first the cylindrically shaped section and then the tapering section.

2. General Background

A number of tibial components have been patented that relate to tibial components having a tray, and a stem portion that provides initial fixation when the prosthesis is implanted.

An example of a modular tibial support is seen in the Elias U.S. Pat. No. 5,246,459 entitled "Modular Tibial Support Pegs for the Tibial Component of a Prosthetic Knee Replacement System". The Elias Patent discloses a modular tibial support peg operable to secure a tibial component of a knee joint prothesis to a tibia having a groove. The modular tibial support peg includes a cylindrical body with a ridged outer surface operable to engage the groove in the tibia. The modular tibial support peg further includes a plurality of spikes extending inferiorly from the cylindrical body. The spikes are operable to engage the tibia at the inferior end of the groove.

U.S. Pat. No. 5,137,536 issued to Tomihisa Koshino describes a tibial component for an artificial knee joint. The tibial component includes a plate section having an upper surface and a pair of bearing surfaces parts that are adapted to be in sliding contact with a femoral component. A stem portion extends downwardly from a lower surface of the plate section. A pair of blade like members extend obliquely and posteriorly from the stem. The plate section has a lower surface with a plurality of elongated grooves for improving affinity with respect to the surrounding bone, the grooves including a first group of grooves and a second set of group of grooves extending perpendicularly to the first group of grooves.

A British Patent 2,192,543A discloses a peg for use in prosthetic devices. A peg of metal or ceramics is defined as being suitable for use as a fixator and/or a bone strengthener in connection with a prosthetic device. The peg has a portion of generally tapered form that increases in cross section from an insertion end. The surface of the tapering end portion has alternating ridges along its length extending therearound, each successive ridge as one moves away from the insertion end having an outer surface spaced by a comparatively small amount at a greater distance from the axis of the peg then the outer surface of the preceding ridge. The peg may be discrete or form a part of a prosthetic device.

U.S. Pat. No. 4,938,769 issued to James Shaw discloses an end bone anchorage assembly for a tibial prosthesis that includes an axially elongated central stem and a plurality of elongated fixation pegs spaced from the stem. The stem and the pegs have proximal and distal ends. The proximal ends of the stem define an attachment table. A plurality of structural links interconnect the pegs and the stem. Means is provided for removably attaching a tibial tray to the assembly wherein each of the pegs is connected to the stem by the structural link.

The Bolesky et al. U.S. Pat. No. 4,479,271 entitled "Prosthetic Device Adapted to Promote Bone/Tissue Ingrowth" discloses a tibial component that includes a table and at least one porous metal stem protruding from the lower base surface of the bottom base layer of the table wherein the outer surface of the protruding stem is adapted to be in direct contact with the prepared bone surface to promote the ingrowth of bone and/or tissue and wherein each of the protruding porous metal stems includes a bore therethrough which extends from the distal end of the stem through the upper surface of the bottom base layer of the table.

The Murray U.S. Pat. No. 4,016,606 discloses a knee prosthesis that includes a tibial component with a tray and with a stem adapted to be received in a longitudinal bore in the patient's femur. The stem has one end that is integral with a depending generally spheroidal surface having generally the same radius as the radius of the spheroidal depression in the insert.

SUMMARY OF THE INVENTION

When implanting a tibial tray (eg. porous or cemented), it is extremely important to get excellent initial fixation. The implant must be able to resist forces that rotate, shear, or tilt the component. The present invention provides an improved stem in modular form, for use with a tibial component and which provides the ability to resist the forces of rotation, shear, and tilt. Thus, the present invention provides an improved tibial prosthesis with excellent initial fixation. The metaphyseal tibial stem of the present invention provides rotational, shear and tilting resistance for an implanted tibial component.

The apparatus of the present invention includes a tibial tray for replacing a portion of the patient's proximal tibia.

The stem has proximal and distal end portions and defines a projection from the under surface of the tray, forming an angle therewith. The stem is provided for anchoring the tibial tray to the proximal tibia.

The stem includes a connection for attaching the stem to the tray in modular fashion. This allows multiple stems of differing size to form a kit that allows the surgeon to select a particular sized stem for connection to the tibial tray that fits the patient best.

The stem includes a generally cylindrically shaped proximal portion and a gradually tapering distal portion. A plurality of longitudinally extending, generally parallel and circumferentially spaced fins extend about the stem and substantially the full length of the stem. Thus, each of the fins tracks the cylindrically shaped proximal portion and then angles to track the gradually tapering portion.

In the preferred embodiment, the gradually tapering distal portion of the stem is conically shaped.

In the preferred embodiment, the fins are preferably equally spaced apart. The stem provides a hollow cylindrical portion with a generally tubular inner bore.

The fins are generally triangularly shaped in transverse cross section.

The proximal and distal sections are integrally joined at a transition portion of the stem in the preferred embodiment.

Each of the fins has an outer edge that includes first and second linear sections that define an obtuse angle therebetween. In the preferred embodiment, this angle is greater than 90 and less than 180 degrees.

Each fin is separated by a longitudinal, generally U-shaped channel.

Each of the fins includes a pair of surfaces extending longitudinally between the proximal and distal ends.

As the fin travels down the tapered cone section, the pair of surfaces of each fin become narrower, resulting in a sharp edge prior to reaching the flat distal tip of the stem. One circumferential portion of the stem can be without fins.

The stem preferable provides a generally flat distal tip that defines the lower end of the stem and the end of the conically shaped portion.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein:

FIG. 5 is a perspective view of the preferred embodiment of the apparatus of the present invention;

FIG. 6 is a sectional view taken along lines 6—6 of FIG. 5;

FIG. 7 is a partial perspective cutaway view of the preferred embodiment of the apparatus of the present invention illustrating the stem portion thereof;

FIG. 8 is another partial perspective cutaway view of the preferred embodiment of the apparatus of the present invention illustrating the stem portion thereof;

FIG. 9 is a partial elevational view of the preferred embodiment of the apparatus of the present invention illustrating various sized and shaped stem portions thereof.

DETAILED DESCRIPTION OF THE PREFERRED EMBODIMENT

Figures 1, 2:
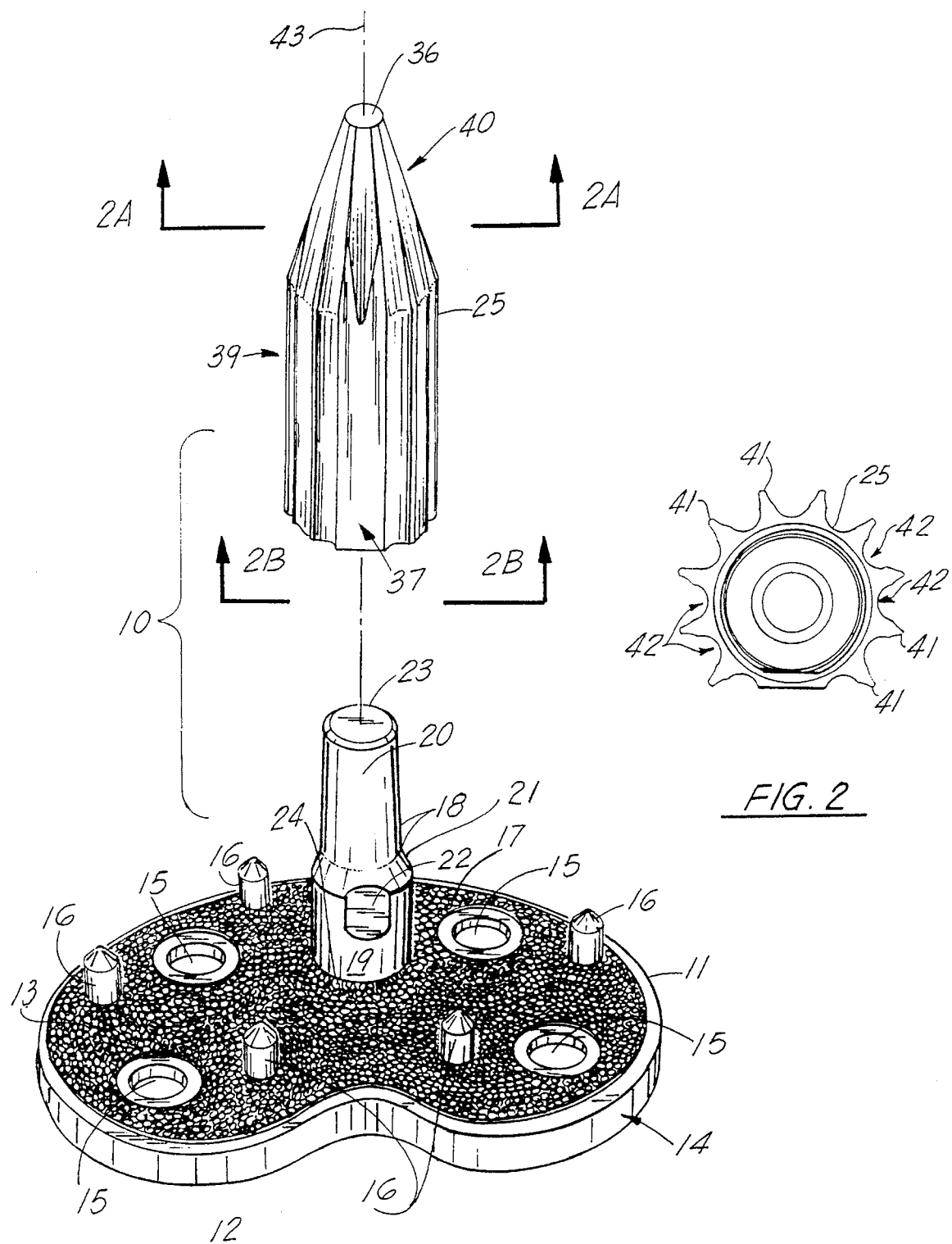
FIG. 1 is a perspective exploded view of the preferred embodiment of the apparatus of the present invention.
FIG. 2 is a fragmentary end view of the stem portion of the preferred embodiment of the apparatus of the present invention.

FIGS. 1–6 illustrate the preferred embodiment of the apparatus of the present invention designated generally by the numeral 10. Tibial prosthesis 10 includes a transversely extending tibial tray 11 having a proximal surface 12 and a distal surface 13. As is known in the art, the distal surface 13 faces the proximal end of the patient's tibia after the proximal end of the patient's tibia has been surgically prepared with a transverse cut. The tibial tray 11 provides a peripheral surface 14 that is shaped to conform to the prepared surface of the proximal tibia.

A plurality of openings 15 can be placed through the tray 11, communicating with both the proximal 12 and distal 13 surfaces. Openings 15 are receptive of one or more bone screws for attaching the prosthesis 10 to the patient's proximal tibia. A plurality of bone spikes 16 extend from distal surface 13 forming an angle therewith, preferably about ninety degrees (90°).

Distal surface 13 can provide a bone attachment surface 17 such as for example a beaded surface. At the central portion of distal surface 13, post 18 extends therefrom at an angle of about ninety degrees (90°). Post 18 includes a larger diameter section 19 and a smaller diameter section 20 that has a taper. An annular conical shoulder 21 defines a transition between larger diameter section 19 and smaller diameter tapered section 20.

Post 18 has a flat surface 22 portion on the outer surface of larger diameter section 19, and extending to annular shoulder 21 as shown in FIG. 1. As will be described more fully hereinafter, flat surface 22 cooperates with a similar flat surface of a modular metaphyseal stem 25 to prevent incorrect assembly of the metaphyseal stem 25 relative to post 18.

Post 18 has a flat circular end portion 23 that defines the distal end of post 18. Post 18 attaches to tibial tray 11 at joint 24 that can be welded for example or post 18 and tray 11 can be machined as one piece. The bone attachment surface 17 can extend over joint 24, and partially to larger diameter section 19.

Metaphyseal stem 25 (FIGS. 1, 2, 2A–2B, 3, 4 and 7–9) provides a proximal end 26 and a distal end 27. Stem 25 has a closed end bore 28. Bore 28 has a closed end portion 29 and an open portion 30. Bore 28 is similarly sized and shaped to post 18 for receiving post 18 upon assembly of metaphyseal stem 25 thereto. Thus, bore 28 provides a larger diameter section 31, an annular shoulder 35 defining a transition section, a small tapered diameter section 32, an annular shoulder 32A defining a transition section, and a conical end portion 33. Internal threads can be provided to closed end portion 29.

The corresponding flat surfaces 22, 34 ensure proper assembly of stem 25 relative to post 18. The corresponding smaller diameter sections 20 and 32 are annular wedge shaped sections that engage upon assembly so that a wedge lock or morse taper lock fit is achieved between stem 25 and post 18 when stem 25 is placed over post 18 and loaded onto post 18 with an impact driver for example. In use, the impact driver would be used to transfer load to metaphyseal stem 25 at flat distal surface 36.

In the preferred embodiment, there can be multiple metaphyseal stems 25A–25C of differing size as shown in FIG. 9. The flat distal surface 36 of the metaphyseal stems 25A–25B shown in FIG. 9 are of a larger diameter than the flat distal surface 36A for the metaphyseal stem 25C shown in FIG. 9.

Each of the flat metaphyseal stems 25 have a longitudinally extending flat surface 37 that begins at proximal end 26 of metaphyseal stem 25 and extends to an annular transition portion 38 of stem 25 as shown in FIGS. 5–6. The annular transition portion 38 is positioned between a generally cylindrical section 39 of metaphyseal stem 25 and a tapering section 40 of metaphyseal stem 25. The tapering section 40 can be frustroconically shaped as shown in FIGS. 1, 3–9.

By providing a cylindrical section 39 of generally constant diameter, the surgeon can drill a cylindrically shaped opening in the patient's cancellous bone tissue to receive stem 25 that is smaller in diameter than the outer diameter of cylindrical section 39. The tapering section 40 first enters the surgically formed opening, registering the metaphyseal stem 25 in the proper location. Thereafter, continued driving of the prosthesis 10 into the patient's tibia causes the plurality of fins 41 to cut into the cancellous bone.

Figure 2B:
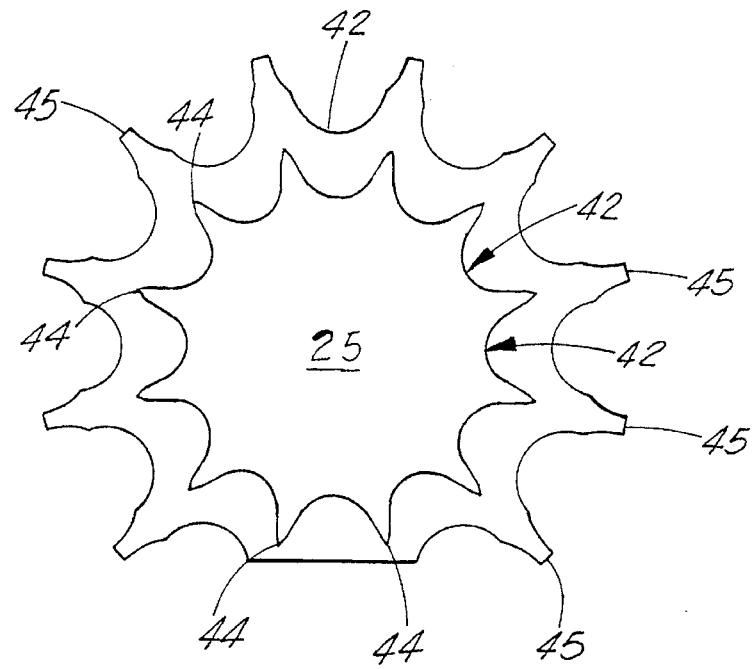
FIG. 2B is a cross section taken along lines 2B—2B of FIG. 1 and including an overlay of FIG. 2A, thus illustrating the tapering of the stem and the changing thickness of the fins.
Figure 2A:
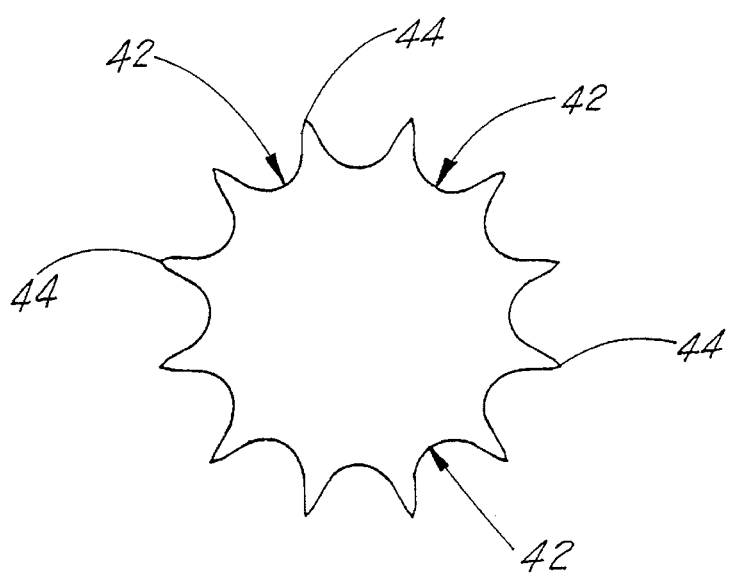
FIG. 2A is a cross section through the conical section of the stem portion taken along lines 2A—2A of FIG. 1.
Figure 3:
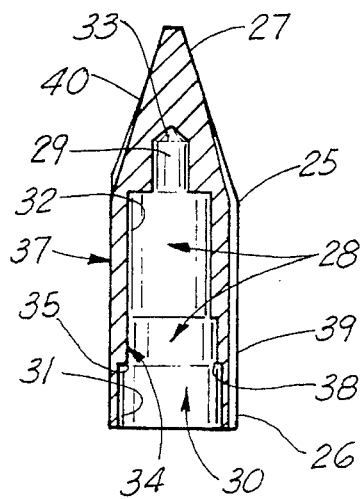
FIG. 3 is fragmentary sectional view of the preferred embodiment of the apparatus of the present invention illustrating the stem portion thereof.
Figure 4:
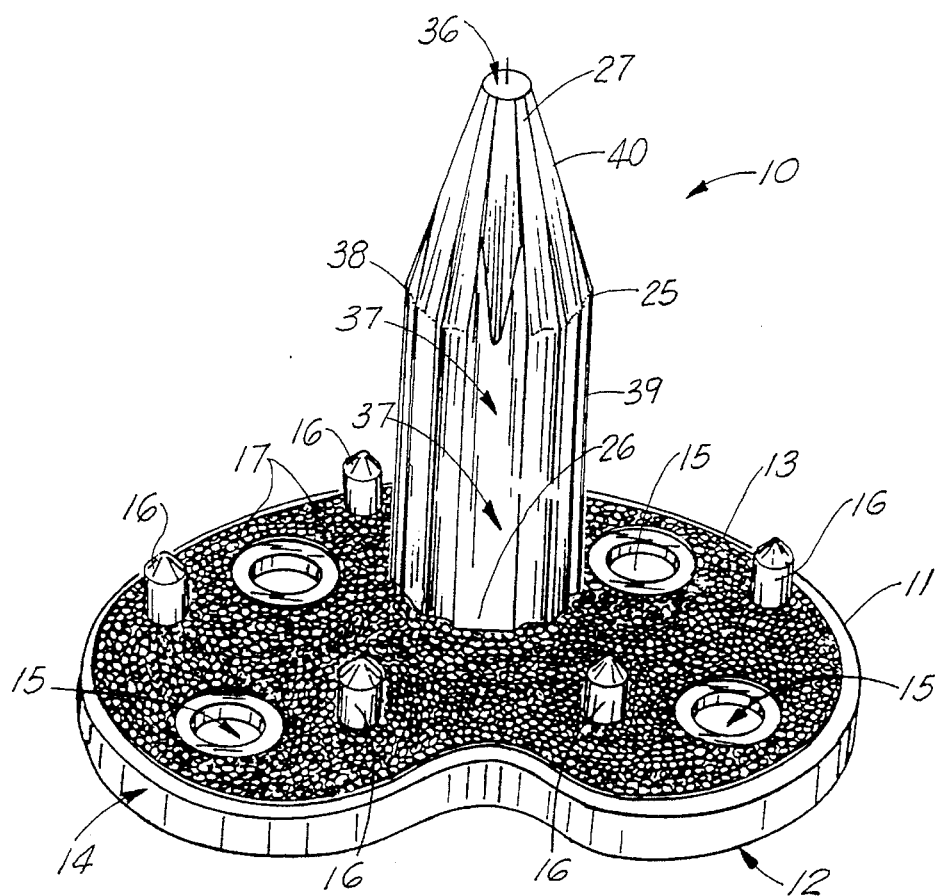
FIG. 4 is a perspective view of the preferred embodiment of the apparatus of the present invention.

A plurality of channels 42 (FIGS. 2, 2A, 2B, 5, 7 and 8) are defined between the plurality of fins 41. Fins 41 are circumferentially spaced and generally parallel to one another. In the preferred embodiment the channels are generally U-shaped, extend longitudinally, and are generally parallel to one another. The fins 41 and channels 42 are circumferentially spaced about the central longitudinal axis of metaphyseal stem 25. In FIGS. 2A–2B fins 41 can be seen as having sharp edges 44 at frustroconical tapering section 40 and blunt edges 45 at cylindrical section 39.

Figure 12:
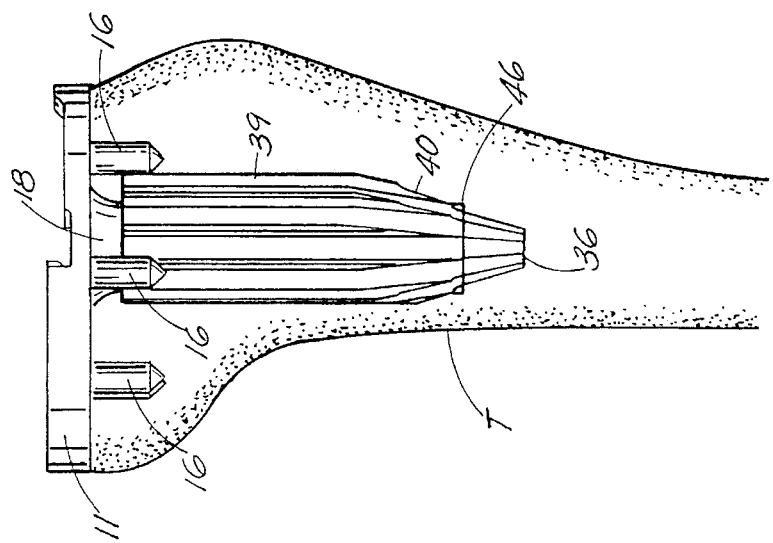
FIGS. 10–12 are schematic elevational views that demonstrate the surgical method of implanting the preferred embodiment of the apparatus of the present invention.
Figure 11:
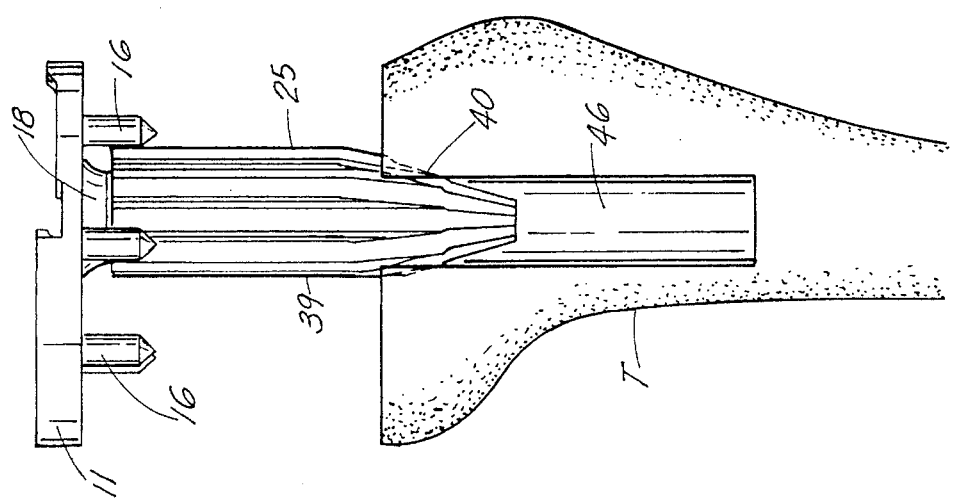
Figure 10:
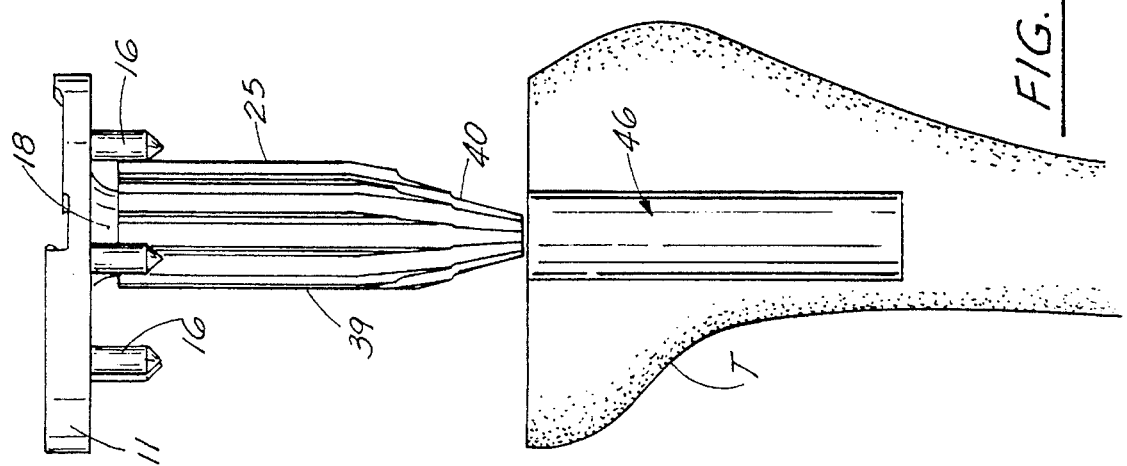

The bone is prepared to receive the metaphyseal stem by punching a plug into the bone (perpendicular to the plane of the cut) that creates a hole 46 that is for example 12–14 mm in diameter and 40–50 mm deep. The device is then driven into this hole as shown in FIGS. 10–12. Notice in FIG. 11 that the hole 46 has a diameter smaller than the diameter of stem cylindrical section 39. This allows the fins 41 to bite into surrounding bone tissue that is adjacent hole 46.

The following table lists the parts numbers and parts descriptions as used herein and in the drawings attached hereto.

PARTS LIST

| Part Number | Description |
| --- | --- |
| 10 | tibial prosthesis |
| 11 | tibial tray |
| 12 | proximal surface |
| 13 | distal surface |
| 14 | peripheral surface |
| 15 | openings |
| 16 | bone spikes |
| 17 | bone attachment surface |
| 18 | post |
| 19 | larger diameter section |
| 20 | smaller diameter tapered section |
| 21 | annular shoulder |
| 22 | flat surface |
| 23 | circular end |
| 24 | joint |
| 25 | metaphyseal stem |
| 25A | metaphyseal stem |
| 25B | metaphyseal stem |
| 25C | metaphyseal stem |
| 26 | proximal end |
| 27 | distal end |
| 28 | bore |
| 29 | closed end of bore |
| 30 | open end of bore |
| 31 | larger diameter section |
| 32 | smaller diameter tapered section |
| 32A | flat annular surface |
| 33 | conical section |
| 34 | flat surface |
| 35 | flat annular surface |
| 36 | flat distal surface |
| 36A | flat distal surface |
| 37 | flat longitudinal surface |
| 38 | annular transition portion |
| 39 | cylindrical section |
| 40 | tapering section |
| 41 | fins |
| 42 | channels |
| 43 | central longitudinal axis |
| 44 | sharp edges |
| 45 | blunt edges |
| 46 | surgically formed opening |
| T | tibia |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A tibial prosthetic knee component comprising:
   a) a tibial tray for replacing a portion of the patient's proximal tibia;
   b) a stem portion having proximal and distal end portions, the stem defining a projection from the tray, forming an angle therewith, for anchoring the tibial tray to the proximal tibia;
   c) the stem including means at the proximal end portion for attachment to the tray and a distal tip at the distal end portion;
   d) the stem comprising a generally cylindrically shaped proximal portion and a conically shaped distal portion;
   e) a plurality of longitudinal extending, generally parallel circumferentially spaced fins extending substantially the length of the stem, the fins communicating with the distal tip;
   f) a plurality of longitudinally extending channels positioned respectively between the fins, the channels gradually deepening and the fins gradually increasing in radial thickness at greater distances from the distal tip at least at the conically shaped distal portion; and
   g) a flat surface of generally constant width extending longitudinally between the proximal and distal ends, said flat surface having edges that are generrlly parallel to said fins.

2. The tibial prosthetic knee component of claim 1 wherein the fins have tips that are sharp at the distal portion of the stem to cut the bone.

3. A tibial prosthetic knee component comprising:
   a) a tibial tray for replacing a portion of the patient's proximal tibia;
   b) a stem portion having proximal and distal end portions, the stem defining a projection from the tray, forming an angle therewith, for anchoring the tibial tray to the proximal tibia;
   c) the stem including means for attachment to the tray;
   d) the stem comprising a generally cylindrically shaped proximal portion and a conically shaped distal portion;
   e) a plurality of longitudinal extending, generally parallel circumferentially spaced fins extending substantially the length of the stem;
   f) wherein the fins have tips that are sharp at the distal portion of the stem to cut the bone, wherein the fin tips become less sharp proximally; and
   g) a flat surface of generally constant width extending longitudinally between the proximal and distal ends, said flat surface having edges that are generally parallel to said fins.

4. The prosthesis of claim 1 wherein the fins are equally spaced apart.

5. The prosthesis of claim 1 wherein the fins extend from a hollow cylindrical portion of the stem having a generally tubular inner bore.

6. The prosthesis of claim 1 wherein the fins are generally triangularly shaped in transverse cross section.

7. The prosthesis of claim 1 wherein the stem is removably attached to the tray.

8. The prosthesis of claim 1 wherein the stem and tray are integral.

9. The prosthesis of claim 1 wherein there are at least 3 fins.

10. The prosthesis of claim 1 wherein the proximal section and distal sections are integrally jointed at a transition portion.

11. The prosthesis of claim 1 wherein each fin has an outer edge that includes first and second linear sections that define an obtuse angle therebetween.

12. The prosthesis of claim 11 wherein the angle is greater than 90 and less than 180 degrees.

13. The prosthesis of claim 1 wherein each fin is separated by a longitudinal channel.

14. The prosthesis of claim 1 wherein the stem further comprises a flat surface of generally constant width extending longitudinally between the proximal and distal ends, said flat surface having edges that are generally parallel to said fins.

15. The prosthesis of claim 1 wherein the stem has a flat distal tip.

16. A tibial prosthetic knee component comprising:
   a) a tibial tray for replacing a portion of the patient's proximal tibia;
   b) a stem portion having proximal and distal end portions, the stem defining a projection from the tray, forming an angle therewith, for anchoring the tibial tray to the proximal tibia;
   c) the stem including gradually tapering distal section and a generally cylindrically shaped section;
   d) a plurality of longitudinal extending, generally parallel circumferentially spaced fins extending substantially the length of the stem;
   e) a plurality of continuous longitudinal channels positioned between the fins and extending substantially the length of the stem, wherein the fins are spaced circumferentially apart about 3 to 180° (3–180 degrees);
   f) the fin height measured from the core diameter of the cylindrical section to the outer edge flat portion of the fin is 2 mm to 40 mm; and
   g) a plurality of longitudinally extending channels positioned respectively between the fins, the channels gradually deepening and the fins gradually increasing in radial thickness at greater distances from the distal tip at least at the conically shaped distal portion.

17. The prosthesis of claim 16 wherein the channels are equally spaced apart.

18. The prosthesis of claim 16 wherein the stem is removably attached to the tray and the fins extend from a hollow cylindrical portion of the stem having a generally tubular inner bore.

19. The prosthesis of claim 16 wherein the fins are generally triangularly shaped in transverse cross section.

20. The prosthesis of claim 16 further comprising taper locking means for removably attaching the stem to the tray.

21. The prosthesis of claim 16 wherein there are at least 3 fins.

22. The prosthesis of claim 16 wherein the proximal section and distal sections are integrally jointed at a transition portion.

23. The prosthesis of claim 16 wherein each fin has an outer edge that includes proximal and distal linear sections that define an obtuse angle therebetween which is greater than 90 and less than 180 degrees.

24. The prosthesis of claim 16 further comprising a longitudinally extending flat surface on the stem.

25. The prosthesis of claim 21 wherein the longitudinal flat surface is between about 0 and 40 mm wide.

26. The prosthesis of claim 16 wherein the flat surface is generally parallel to the fins.

27. The prosthesis of claim 16 wherein the stem has a flat distal tip.

28. A tibial prosthetic knee component comprising:
   a) a tibial tray for replacing a portion of the patient's proximal tibia;
   b) a stem portion having proximal and distal end portions, the stem defining a projection from the tray, forming an angle therewith, for anchoring the tibial tray to the proximal tibia;
   c) the stem comprising a generally cylindrically shaped proximal portion and a gradually tapering distal portion;
   d) a plurality of longitudinal extending, generally parallel circumferentially spaced fins extending substantially the length of the stem;
   e) a plurality of continuous longitudinal channels positioned between the fins and extending substantially the length of the stem, wherein the fins are spaced circumferentially apart about 3° to 180° (3–180 degrees);
   f) the fin height measured from the core diameter of the cylindrical section to the outer edge flat portion of the fin is 2 mm to 40 mm; and
   g) a plurality of longitudinally extending channels positioned respectively between the fins, the channels gradually deepening and the fins gradually increasing in radial thickness at greater distances from the distal tip at least at the conically shaped distal portion.

29. A tibial prosthetic knee component comprising:
   a) a tibial tray for replacing a portion of the patient's proximal tibia;
   b) a stem portion having proximal and distal end portions, the stem defining a projection from the tray, forming an angle therewith, for anchoring the tibial tray to the proximal tibia;
   c) the stem including gradually tapering distal section and a generally cylindrically shaped section;
   d) a plurality of longitudinal extending, generally parallel circumferentially spaced fins extending substantially the length of the stem;
   e) a plurality of continuous longitudinal channels positioned between the fins and extending substantially the length of the stem, wherein the fins are spaced circumferentially apart about 3° to 180° (3–180 degrees);
   f) the fin height measured from the core diameter of the cylindrical section to the outer edge flat portion of the fin is 2 mm to 40 mm;
   g) a plurality of longitudinally extending channels positioned respectively between the fins, the channels gradually deepening and the fins gradually increasing in radial thickness at greater distances from the distal tip at least at the conically shaped distal portion;
   h) a flat surface of generally constant width extending longitudinally between the proximal and distal ends, said flat surface having edges that are generally parallel to said fins.

30. A tibial prosthetic knee component comprising:
   a) a tibial tray for replacing a portion of the patient's proximal tibia;
   b) a stem portion having proximal and distal end portions, the stem defining a projection from the tray, forming an angle therewith, for anchoring the tibial tray to the proximal tibia;

c) the stem comprising a generally cylindrically shaped proximal portion and a gradually tapering distal portion;

d) a plurality of longitudinal extending, generally parallel circumferentially spaced fins extending substantially the length of the stem;

e) a plurality of continuous longitudinal channels positioned between the fins and extending substantially the length of the stem, wherein the fins are spaced circumferentially apart about 3° to 180° (3–180 degrees);

f) the fin height measured from the core diameter of the cylindrical section to the outer edge flat portion of the fin is 2 mm to 40 mm;

g) a plurality of longitudinally extending channels positioned respectively between the fins, the channels gradually deepening and the fins gradually increasing in radial thickness at greater distances from the distal tip at least at the conically shaped distal portion;

h) a flat surface of generally constant width extending longitudinally between the proximal and distal ends, said flat surface having edges that are generally parallel to said fins.

31. A tibial prosthetic knee component comprising:

a) a tibial tray for replacing a portion of the patient's proximal tibia;

b) a stem portion having proximal and distal end portions, the stem defining a projection from the tray forming an angle therewith, for anchoring the tibial tray to the patient's proximal tibia;

c) the stem being removably attached to the tray;

d) the stem including a generally cylindrically-shaped proximal section and a tapered distal section with a pointed distal tip;

e) a plurality of longitudinal extending, generally parallel circumferentially spaced fins extending substantially the length of the stem, the fins communicating with the distal tip;

f) a plurality of longitudinally extending channels positioned respectively between the fins, the channels gradually deepening and the fins gradually increasing in radial thickness at greater distances from the distal tip at least at the conically shaped distal section; and g) wherein the fins have edges that vary in sharpness between the ends of the stem.

32. The prosthesis of claim 31 wherein the stem further comprises a flat surface of generally constant width extending longitudinally between the proximal and distal ends, said flat surface having edges that are generally parallel to said fins.

33. A tibial prosthetic knee component comprising:

a) a tibial tray for replacing a portion of the patient's proximal tibia;

b) a stem portion having proximal and distal end portions, the stem defining a projection from the tray, forming an angle therewith, for anchoring the tibial tray to the proximal tibia;

c) the stem including means for attachment to the tray;

d) the stem comprising a generally cylindrically shaped proximal portion and a conically shaped distal portion;

e) a plurality of longitudinal extending, generally parallel circumferentially spaced fins extending substantially the length of the stem; and f) wherein the fins have tips that are sharp at the distal portion of the stem to cut the bone, wherein the fin tips become less sharp proximally.

* * * * *

UNITED STATES PATENT AND TRADEMARK OFFICE
CERTIFICATE OF CORRECTION

PATENT NO. : 5,609,641
DATED : Mar. 11, 1997
INVENTOR(S) : Chris E. Johnson, Thomas A. Carls, both of Memphis; David L. Evans, Bartlett, all of Tenn.

It is certified that error appears in the above-identified patent and that said Letters Patent is hereby corrected as shown below:

On the title page, insert item

[75] Inventors: Chris E. Johnson, Thomas A. Carls, both of Memphis; David L. Evans, Bartlett, all of Tenn; and Leo A. Whiteside, of St. Louis, MO.

Signed and Sealed this

Twenty-third Day of December, 1997

Attest:

BRUCE LEHMAN

Attesting Officer

Commissioner of Patents and Trademarks